United States Patent
Inokuti

(10) Patent No.: US 6,462,340 B1
(45) Date of Patent: Oct. 8, 2002

(54) DEVICE FOR MEASURING CRYSTAL ORIENTATION AND CRYSTAL DISTORTION IN POLYCRYSTALLINE MATERIALS

(75) Inventor: Yukio Inokuti, Chiba (JP)

(73) Assignee: Kawasaki Steel Corporation, Kobe (JP)

( * ) Notice: Subject to any disclaimer, the term of this patent is extended or adjusted under 35 U.S.C. 154(b) by 209 days.

(21) Appl. No.: 09/691,195

(22) Filed: Oct. 19, 2000

(30) Foreign Application Priority Data

Oct. 27, 1999 (JP) .......................................... 11-304865

(51) Int. Cl.[7] .......................... H01J 37/295; G01N 23/20
(52) U.S. Cl. ........................................ 250/310; 250/397
(58) Field of Search .................................. 250/310, 397

(56) References Cited

U.S. PATENT DOCUMENTS

| | | | |
|---|---|---|---|
| 3,848,126 A | * 11/1974 | Swindells et al. | 250/310 |
| 5,557,104 A | * 9/1996 | Field et al. | 250/310 |
| 6,326,619 B1 | * 12/2001 | Michael et al. | 250/310 |

FOREIGN PATENT DOCUMENTS

| | | |
|---|---|---|
| JP | 6-22108 | 1/1994 |
| JP | 6-86141 | 3/1994 |
| JP | 7-9564 | 1/1995 |
| JP | A-7-77504 | 3/1995 |
| JP | 1-068703 | 3/1998 |
| JP | A-10-239255 | 9/1998 |

OTHER PUBLICATIONS

"A New Method for Local Crystal Orientation Analysis" Yoshimitsu Iwasaki et al., Proceedings of the Japanese Metal Society Meetings, 18, 1979, pp. 632–636.

"Material Characteristics and Control of Crystal Orientation Distribution in Polycrystalline Materials" Youichi Ishida, Japanese Metal Society Seminar, Jul. 1992, pp. 7–12.

* cited by examiner

Primary Examiner—Jack Berman
(74) Attorney, Agent, or Firm—Oliff & Berridge PLC

(57) ABSTRACT

A compact device for measuring crystal orientation and crystal distortion in polycrystalline materials is disclosed. The device includes a focused electron beam generator unit, a sample holder, an electron beam detector, a Kossel X-rays detector, an image processor, and a display. The device employs the Kossel X-rays reflection method to measure crystal distortion and to measure crystal orientation in the inner portion of polycrystalline materials, slightly deeper than the shallow surface, while employing the electron beam diffraction method to measure crystal orientation at the shallow surface.

14 Claims, 4 Drawing Sheets

DEVICE FOR MEASURING CRYSTAL ORIENTATION AND CRYSTAL DISTORTION IN POLYCRYSTALLINE MATERIALS

BACKGROUND OF THE INVENTION

1. Field of Invention

The invention relates to devices for measuring crystal orientation and crystal distortion in polycrystalline materials.

2. Description of Related Art

The Laue X-ray method has conventionally been used to measure the crystal orientation of metallic materials, ceramics, rocks and the like. In addition, the Kossel X-rays method has commonly been used to measure distortion introduced in crystals (hereinafter referred to as "crystal distortion"). These methods, however, disadvantageously target crystal grains on the order of several millimeters or larger, and they are not applicable to minute crystal grains on the order of 5 to 20 $\mu$m, which constitute common metallic materials.

Accordingly, the crystal orientation of such minute crystal grains has typically been measured and analyzed as a formation texture, by using, for example, polar diagrams. This approach, however, only determines the average crystal orientation of a large number of crystal grains. Thus, this approach did not substantially contribute to research and development in the field of secondary recrystallization. In secondary recrystallization, detailed information is required for each crystal grain, not information on averages, because only one out of every two million crystal grains becomes the nucleus for secondary crystallization.

In the 1970s, the Kossel X-rays transmission method, the Kossel X-rays reflection method, and the electron channeling pattern method (also referred to as the Kikuchi line method), which all employ electron beams, were developed as alternatives to the Laue X-rays method and the Kossel X-rays method. These newly developed methods enabled detection of crystal orientation and crystal distortion in minute crystal grains on the order of 5 to 20 $\mu$m.

Furthermore, the development of computers and image analysis techniques enabled automated analysis of crystal orientation and crystal distortion for large numbers of minute crystal grains. The mapping of the analysis results allowed further analysis on nucleation and selective growth of the crystal grains, and colored mapping S allowed visualization of the generation and distribution of complex crystal grains composed of two or more elements. These features are disclosed in Japanese Patent Publications Nos. Hei 7-9564 and Hei 6-86141.

In the Kossel X-rays reflection method, a focused electron beam is emitted onto a bulk sample, Kossel X-rays generated within a pyriform area from approximately a depth of 0.5 $\mu$m in the bulk sample are detected, and crystal orientation and crystal distortion in the bulk sample are calculated based on the diffraction pattern. The details of the Kossel X-rays reflection method are described in "A New Method for Local Crystal Orientation Analysis" (Yoshimitsu Iwasaki et al., Proceedings of the Japanese Metal Society Meeting, 18, 1979, p. 632)

Kossel X-rays are formed by weak divergent X-rays caused by irradiating crystal grains with an electron beam or X-rays, characteristic X-rays thereby being generated in the bulk sample. In the Kossel X-rays reflection method, however, continuous X-rays, reflected electron beams, and secondary electron beams are generated together with the Kossel X-rays, making it very difficult to extract the Kossel X-rays.

Japanese Patent Publication No. Hei 6-22108 proposes a particular type of thin-film filter disposed between a bulk sample and a Kossel X-rays detector. The filter is an iron thin film on which one of Fe, Mn, Cr, V, Ti and the like is deposited.

Japanese Unexamined Patent Application Publication No. Hei 10-68703 proposes a filter composed of beryllium, disposed in front of a Kossel X-rays detector in order to more effectively reduce negative effects of visible light and undesirable electron beams.

FIG. 1 shows an exemplary Kossel X-rays reflection device. As shown, the device structure and operation includes a focused electron beam 1, reflected electron beams and X-rays 1', a bulk sample 2, a sample holder 20, a filter 3 composed of beryllium, Kossel X-rays 1", a phosphor 4 composed of a phosphorous compound, glass fibers 5 (the phosphor 4 and the glass fibers 5 constituting a phosphor unit 6), a detector 7 implemented by a CCD camera, an image processing unit 8, a display unit 9 (the image processing unit 8 and the display unit 9 constituting an image analysis device 10), and a filter 11 composed of iron.

In order to obtain Kossel X-rays of sufficient intensity, the focused electron beam current is usually about several microamperes. In addition, in order to enhance the accuracy of Kossel X-rays detection and also to minimize effects of background radiation, the gap between the bulk sample 2 and the detector 7 is determined in accordance with the electron beam current. The distance between the bulk sample 2 and the beryllium filter 3 may be varied from approximately 9 to 15 cm. The Kossel X-rays reflection device is disadvantageously larger than the electron beam diffraction device primarily due to this gap. Another disadvantage of the Kossel X-rays reflection device is that, because it must detect weak X-rays, it takes about 40 seconds on average to measure one crystal grain.

Another method of analyzing crystal orientation and crystal distortion of minute crystal grains is the electron beam diffraction method such as, for example, the electron channeling pattern (ECP) method using the Kikuchi pattern. The details of the method are described in "Material Characteristics and Control of Crystal Orientation Distribution in Polycrystalline Materials" (Youichi Ishida, Japanese Metal Society Seminar, July 1992, pp. 7–12).

Recently, it has been reported that TexSEM Laboratories, Inc. of the United States has developed an electron beam diffraction technique that employs electron back-scatter diffraction, a modification of the method based on the Kikuchi pattern, to measure and analyze crystal orientation of minute crystal grains in a very short time. It has also been reported that Oxford, Inc. of the United Kingdom and Noran Instruments, Inc. of the United States have also developed similar devices, which are sold as TexSEM Laboratories, Inc.

The electron beam diffraction method has the following features.

(1) The capability of measurement of small areas on the order of 0.2 $\mu$m due to the use of extremely narrow electron beams with high voltage and small current (on the order of several nanoamperes).

(2) The capability of measurements in the superficial layer on the order of 0.05 $\mu$m or less in depth.

(3) A high accuracy of ±1° in crystal orientation analysis can be achieved.

(4) Automated analysis that allows rapid measurement of approximately 0.3 to 1.5 seconds for each measured area, and the display of a polar diagram. Usually, more than ten thousands areas can be measured in a few hours.

Because the electron beam current is small, the gap between a sample and the detector can also be made small. Therefore, the electron beam diffraction device can be made more compact than can the Kossel X-rays device.

However, because electron beams penetrate no deeper than the shallow surface, the following problems arise.

(a) In preparing a sample, the sample surface must be treated with special care in order to prevent oxidation and distortion of the surface.

(b) It is not possible to obtain information concerning inner portions just below the shallow surface.

(c) Crystal distortion data is less accurate than in the Kossel X-rays reflection method.

As described above, the Kossel X-rays reflection method and the electron beam diffraction method both have their respective advantages and disadvantages. Each of these methods is unable to achieve quick and accurate measurement of both crystal orientation and crystal distortion.

SUMMARY OF THE INVENTION

Accordingly, it is an object of this invention to provide a compact device for measuring crystal orientation and crystal distortion in polycrystalline materials, in which measurement time is reduced and measurement accuracy is enhanced.

To achieve this object, this invention provides a device for measuring crystal orientation and crystal distortion in polycrystalline materials. The device includes a focused electron beam generator, a sample holder, an electron beam detector, a Kossel X-rays detector, an image processor and a display. Preferably, the electron beam detector includes an electron beam receiving surface, a phosphor element and a detector. The Kossel X-rays detector preferably includes a Kossel X-rays receiving surface, a phosphor element and a detector. Preferably, the electron beam detector and the Kossel X-rays detector share a common phosphor element and a common detector. In embodiments, the electron beam receiving surface and the Kossel X-rays receiving surface are switched from one to the other so that one of the receiving surfaces is used depending on which mode is being employed. The device may further include a filter, composed of either an ultrathin beryllium foil or an ultrathin vapor-deposited beryllium film, disposed over the Kossel X-rays receiving surface.

This invention employs the Kossel X-rays reflection method to measure crystal distortion, and crystal orientation of the inner portion of a sample, slightly deeper than the shallow surface, and also employs the electron beam diffraction method to measure crystal orientation of the shallow surface of the sample.

By incorporating the use of both methods, and by incorporating a filter for extracting Kossel X-rays, this invention provides a compact device that can achieve reduced measurement time and enhanced measurement accuracy.

DETAILED DESCRIPTION OF PREFERRED EMBODIMENTS

The inventors have discovered that, in order to accurately and quickly detect crystal orientation and crystal distortion in polycrystalline materials, it is highly effective to employ the Kossel X-rays reflection method to measure crystal distortion, and to measure crystal orientation in inner portions of a sample, slightly deeper than a shallow surface, and to also employ the electron beam diffraction method to measure crystal orientation at the shallow surface of the sample. Accordingly, the inventors have developed a dual-function device which employs both the Kossel X-rays reflection method and the electron beam diffraction method for simultaneously measuring crystal orientation and crystal distortion of minute crystal grains. In developing the device, the inventors have also found that a filter composed of either an ultrathin beryllium foil, or an ultrathin vapor-deposited beryllium film, disposed between a sample and a detector when using the Kossel X-rays reflection method, reduces measurement time and also allows more compact construction of the device.

An exemplary embodiment of this invention will now be described with reference to the accompanying drawings.

Figure 2:
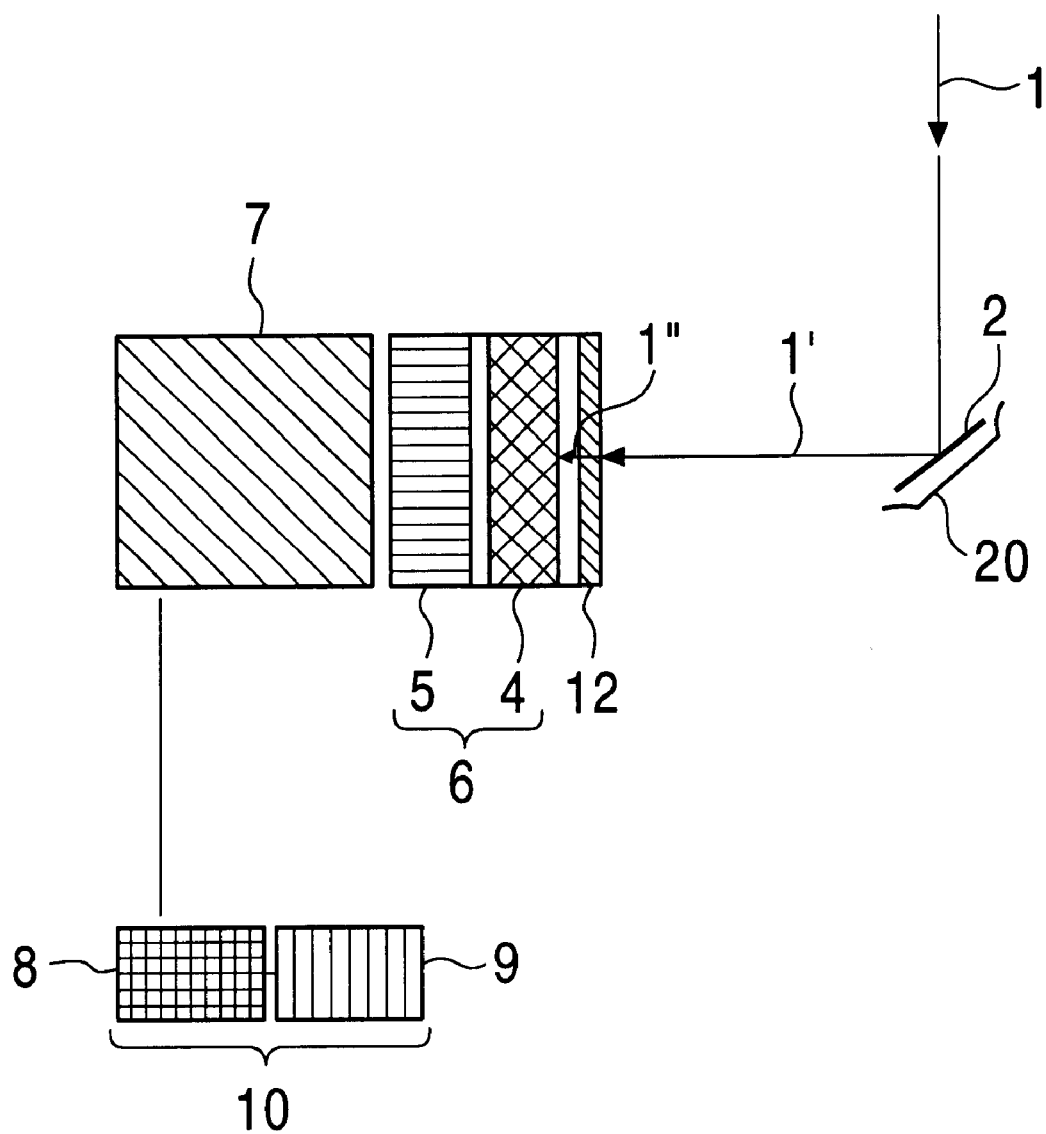
FIG. 2 is a schematic diagram of an exemplary embodiment of a device for measuring crystal orientation and crystal distortion according to this invention.

FIG. 2 shows a measurement device according to an exemplary embodiment of this invention when the Kossel X-rays reflection method is being used. The reflected Kossel X-rays 1" and electron beams from the sample 2 supported by a sample holder 20 in response to irradiation by electron beams are filtered through a filter 12, such that the reflected Kossel X-rays are extracted. The emitted electron beam is of the type commonly used in electron beam diffraction methods, and is narrower and generates less current compared with those commonly used in the Kossel X-rays reflection method. The filter 12 is composed of either an ultrathin beryllium foil, or an ultrathin beryllium vapor-deposited film. The reflected Kossel X-rays are converted into visible light via a phosphor element 6 including a phosphor 4 and glass fibers 5, and then are detected by a detector 7, implemented by a CCD camera. The measurement data is input to the image processor 8 via an interface, and is accumulated for a predetermined period, so that a diffraction image is formed on a display 9. The image processor 8 and the display 9 constitute an image analysis apparatus 10. Crystal orientation and crystal distortion can be calculated by analyzing the pattern and line divergence of the diffraction image. The crystal orientation and crystal distortion, as required, can be mapped in color on the display 9.

Figure 5:
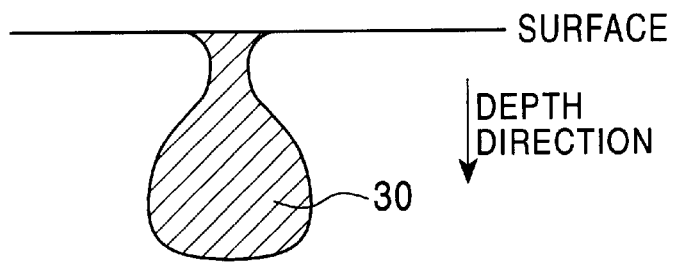
FIG. 5 is a sectional view of a sample, showing an area of the sample where crystal orientation and crystal distortion can be measured in one measurement by the Kossel X-rays reflection method.
Figure 6:
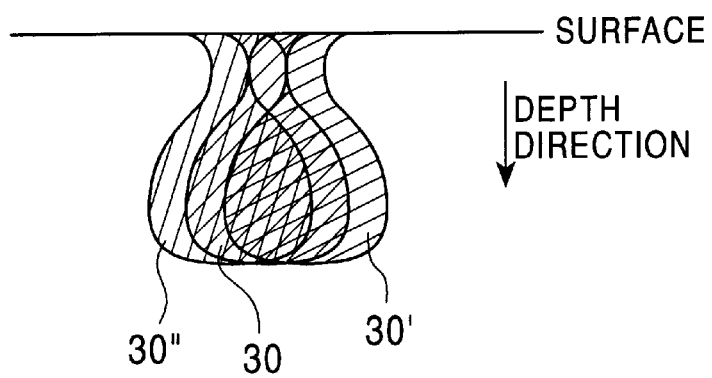
FIG. 6 is sectional view of a sample, showing an area of the sample where crystal orientation and crystal distortion can be measured in a series of measurements by the Kossel X-rays reflection method.

The above method, however, only covers the shaded pyriform-shaped area in FIG. 5. Therefore, in order to obtain information over the entire surface area, measurements must be repeated while changing measurement positions as indicated by 30, 30', and 30'' in FIG. 6. Thus, because multiple measurements are needed, the measurements are time-consuming.

Figure 7:
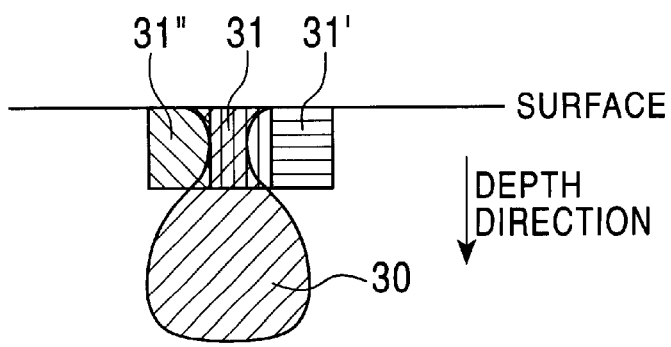
FIG. 7 is a sectional view showing an area of a sample where crystal orientation and crystal distortion can both be measured by using the Kossel X-rays reflection method and the electron beam diffraction method.

In contrast, this invention employs the electron beam diffraction method for the shallow surface (superficial layer). Referring to FIG. 7, this invention employs the Kossel X-rays reflection method for the area 30 while also employing the electron diffraction method for the area 31, 31', and 31''.

Figure 3:
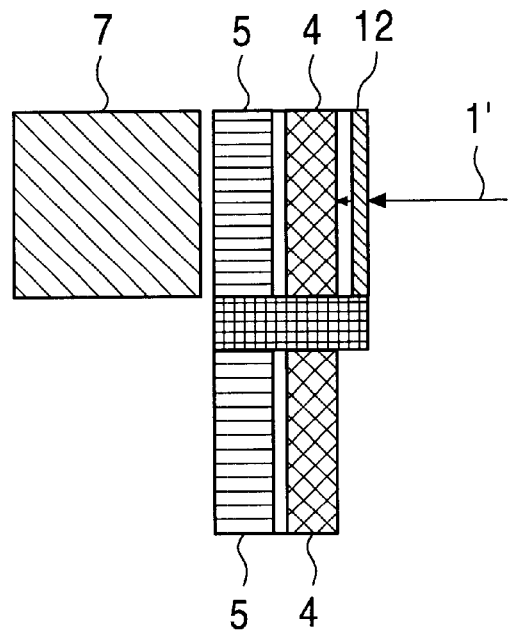
FIG. 3 is a schematic diagram of an exemplary detector in this invention, when a Kossel X-rays receiving surface is being used.
Figure 4:
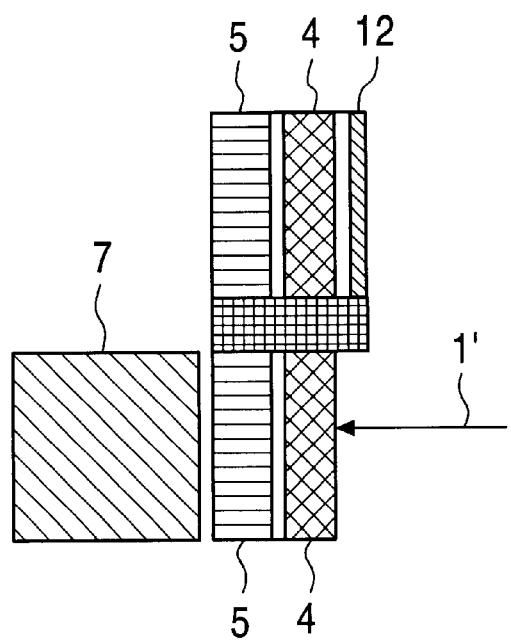
FIG. 4 is a schematic diagram of an exemplary detector in this invention, when an electron beam receiving surface is being used.

FIG. 3 shows the Kossel X-rays receiving surface of a Kossel X-rays detector unit when the Kossel X-rays reflection method is being used in this invention. The same reference numbers are used in FIG. 3 as in FIG. 2. When the Kossel X-rays reflection method is being used, the Kossel X-rays receiving surface (the portion covered by a filter 12 composed of an ultrathin beryllium foil or an ultrathin vapor-deposited beryllium film) is excited.

On the other hand, when the electron beam diffraction method is being used in this invention, the electron beam receiving surface (the portion not covered by the filter 12) is excited.

In the electron beam diffraction method, in a manner similar to that in the Kossel X-rays reflection method, electron beams generated from within the sample are converted into visible light via the phosphor 4 and the glass fibers 5, and the light is then detected by the detector 7. The measurement data is input to the image processor 8 via an interface, and is accumulated for a predetermined period, so that a diffraction image is formed. Crystal orientation can be calculated by analyzing the diffraction image and by comparing it with existing patterns. The crystal orientation can be mapped in color as required.

It is also possible to accumulate measurement data for both the Kossel X-rays reflection line method and the electron beam diffraction method and to perform image processing on the detection data so as to form diffraction images. This allows simultaneous calculation of crystal orientation and crystal distortion.

In this invention, electron beams of the type commonly used in electron beam diffraction are used for the Kossel reflection method as well. The acceleration voltage of the electron beams is on the order of 20 to 50 kV, which is as large as the acceleration voltage of the type of electron beams used in a conventional Kossel X-rays reflection device. However, the electron beam current is on the order of several nanoamperes, which is less than the several microamperes in a conventional Kossel X-rays reflection device. The application of small-current electron beams to the Kossel X-rays device has been made possible due to developments in electron beam diffraction techniques, particularly in enhanced electron beam focusing and image processing capabilities. In this embodiment, the gap between the bulk sample 2 and the filter 12 may range from 2 to 7 cm and may be, for example, 5 cm. Thus, the gap is reduced to one-half or less of the gap in conventional devices, allowing a more compact construction of the device of this invention.

Figure 1:
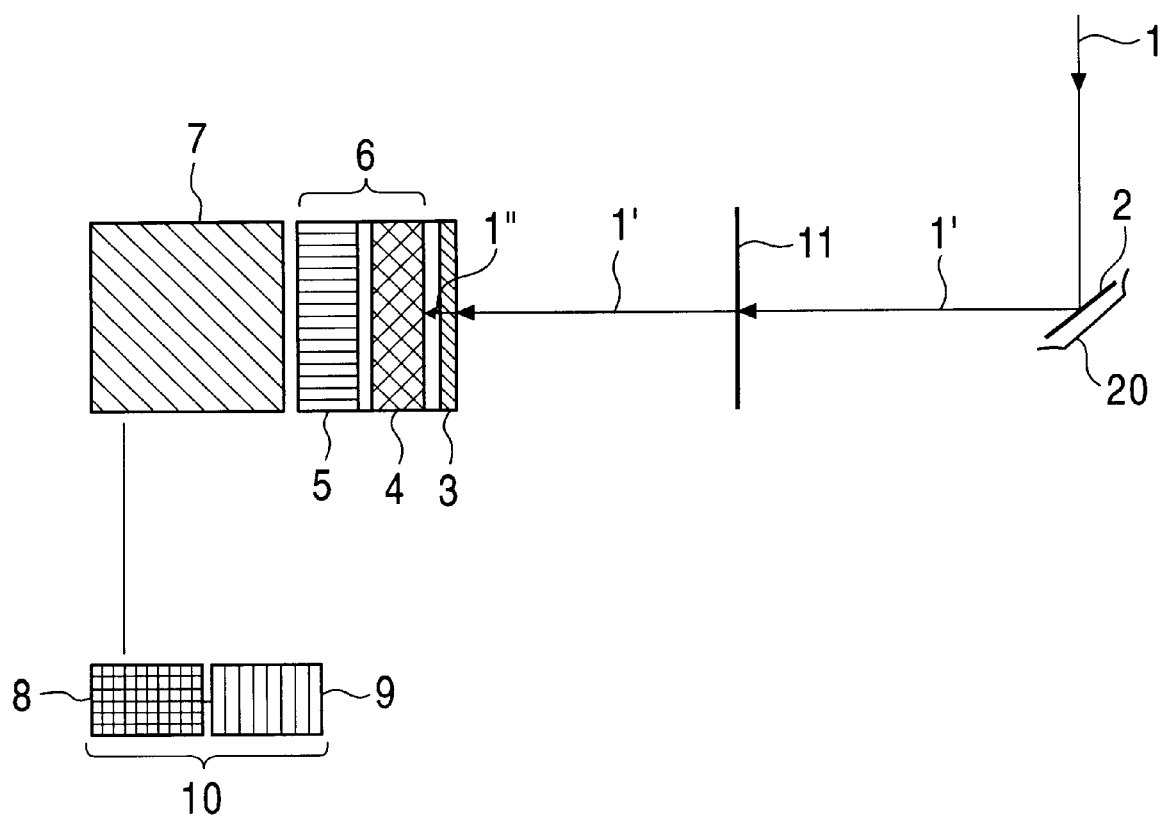
FIG. 1 is a schematic diagram of a diffraction device employing the conventional Kossel X-rays reflection method.

In addition, this invention employs a filter 12 as shown in FIG. 2, which is either an ultrathin beryllium foil or an ultrathin, vapor-deposited beryllium film, instead of the filter 11 composed of iron and the film 3 composed of beryllium as in the conventional device shown in FIG. 1, which are disposed in the transmission path of the X-rays.

The filter 12 is incorporated in the device to block background radiation, including visible light, as much as possible, and to thereby allow extraction of Kossel X-rays, which are weak.

The transmittance of a filter is expressed by the equation:

$$T = \exp(-\alpha \cdot \rho \cdot t)$$

where $\alpha$ is the absorption factor (cm$^2$/g), $\rho$ is the density (g/cm$^3$), and t is the thickness (cm) of the filter.

Based on detailed research by the inventors, it has been discovered that when an electron beam is emitted onto a sample in accordance with typical conditions of electron diffraction, the use of beryllium as a filter, having a thickness of about 0.3 to 30 $\mu$m, allows detection of the weak Kossel X-rays.

The thickness of the filter is reduced to be as small as $\frac{1}{50}$ to $\frac{1}{1000}$ of the thickness of the beryllium film, typically 200 to 500 $\mu$m, used in a conventional Kossel X-rays reflection device.

Beryllium is such a brittle material that fabrication of a beryllium foil is very difficult. Thus, instead of fabricating the filter separately, the filter may be fabricated by depositing beryllium on the phosphorus compound. Additionally, the glass fibers may also be fabricated integrally with the filter 12.

Preferably, the filter is fabricated by depositing a thin beryllium film, having a thickness on the order of 7 $\mu$m, on a phosphor composed of a phosphorous compound, using an ion sputtering technique with a high rate of ionization. The high rate of ionization allows fabrication of a smooth, dense foil. Alternatively, the filter may be fabricated by rolling a beryllium film having a thickness on the order of 200 to 300 $\mu$m, and by mechanically or electrically polishing the rolled film. This method allows fabrication of thin beryllium films having a thickness on the order of 5 to 10 $\mu$m.

In the above-described embodiment, the Kossel X-rays receiving surface and the electron beam receiving surface are switched from one to the other by using a corresponding portion of the phosphor element, either the portion covered by the beryllium filter or the portion not covered by the beryllium filter. Alternatively, the arrangement may be such that only the beryllium filter is used, or is not used.

The device may also incorporate an X-ray analysis device that uses a technique such as Energy Dispersive of X-ray Spectroscopy (EDX or EDS) because of the use of X-rays. As a result, the analysis of alloy components or inclusions near the material surface is possible.

The image processing and color mapping by the image analysis device 10 is performed as follows. Initially, a crystal orientation represented by the polar coordinate system is converted to a crystal orientation represented in the reverse polar coordinate indication, another three-dimensional coordinate system which uses a basic stereographic triangle by stereographic projection, and then a corresponding coordinate value is calculated. The coordinate value is input as the color information of a crystal grain boundary image which has been stored as digitized information in the image memory. The displayed image is characterized by arcuate lines in the case of X-rays, while it is characterized by straight lines in the case of electron beams.

By the image processing and color mapping, the distribution of crystal orientation is displayed in detail, quickly and accurately, so as to aid intuitive understanding. Such a display has previously been obtained only through laborious processes that were conventionally required.

The color information is determined, from the crystal orientation represented in the reverse polar coordinate indication, by the following procedure. Initially, the three primary colors, blue, red, and green, are assigned to three reference points of the reverse polar coordinate system, the reference points being the apexes of the basic stereographic triangle. For a given crystal orientation, the levels of blue, red, and green are calculated in accordance with a color mixing function expressed by C=bB+rR+gG. The levels are input to the blue, red, and green color memories in the image memory as digitized electric signals. The electric signals are sent to a CRT display corresponding to the color memories, so as to display a corresponding image thereon.

The device according to this invention takes only approximately one second for the Kossel X-rays reflection measurement, only approximately 0.3 second for the electron beam diffraction measurement, and some additional switching time. Thus, the measurement time of the invention is significantly reduced from the approximately 45 seconds required in a conventional Kossel X-rays device.

What is claimed is:

1. A device for measuring crystal orientation and crystal distortion in polycrystalline materials, the device comprising:
   a focused electron beam generator;
   a sample holder for holding a sample of polycrystalline material;
   an electron beam detector;
   a Kossel X-rays detector;
   an image processor; and
   a display.

2. The device according to claim 1, wherein:
   the electron beam detector comprises:
      an electron beam receiving surface;
      a phosphor element; and
      a detector; and
   wherein the Kossel X-rays detector comprises:
      a Kossel X-rays receiving surface;
      a phosphor element; and
      a detector.

3. The device according to claim 2, wherein:
   the electron beam detector and the Kossel X-rays detector comprise a common phosphor element and a common detector; and
   the electron beam receiving surface and the Kossel X-rays receiving surface are switched from one to the other so that one of the electron beam receiving surface and Kossel X-ray receiving surface is used.

4. The device according to claim 2, further comprising a filter composed of an ultrathin beryllium foil, wherein the filter is disposed over the Kossel X-rays receiving surface.

5. The device according to claim 3, further comprising a filter composed of an ultrathin beryllium foil, wherein the filter is disposed over the Kossel X-rays receiving surface.

6. The device according to claim 2, further comprising a filter composed of an ultrathin vapor-deposited beryllium film, wherein the filter is disposed over the Kossel X-rays receiving surface.

7. The device according to claim 3, further comprising a filter composed of an ultrathin vapor-deposited beryllium film, wherein the filter is disposed over the Kossel X-rays receiving surface.

8. A method of measuring crystal orientation and crystal distortion in a polycrystalline material, comprising:
   providing the device according to claim 1; and
   measuring the crystal orientation and crystal distortion in the polycrystalline material using the device.

9. A method of measuring crystal orientation and crystal distortion in a polycrystalline material, comprising:
   providing the device according to claim 2; and
   measuring the crystal orientation and crystal distortion in the polycrystalline material using the device.

10. A method of measuring crystal orientation and crystal distortion in a polycrystalline material, comprising:
    providing the device according to claim 3; and
    measuring the crystal orientation and crystal distortion in the polycrystalline material using the device.

11. A method of measuring crystal orientation and crystal distortion in a polycrystalline material, comprising:
    providing the device according to claim 4; and
    measuring the crystal orientation and crystal distortion in the polycrystalline material using the device.

12. A method of measuring crystal orientation and crystal distortion in a polycrystalline material, comprising:
    providing the device according to claim 5; and
    measuring the crystal orientation and crystal distortion in the polycrystalline material using the device.

13. A method of measuring crystal orientation and crystal distortion in a polycrystalline material, comprising:
    providing the device according to claim 6; and
    measuring the crystal orientation and crystal distortion in the polycrystalline material using the device.

14. A method of measuring crystal orientation and crystal distortion in a polycrystalline material, comprising:
    providing the device according to claim 7; and
    measuring the crystal orientation and crystal distortion in the polycrystalline material using the device.

* * * * *